United States Patent [19]

Takeichi et al.

[11] Patent Number: 5,779,935
[45] Date of Patent: Jul. 14, 1998

[54] FERROELECTRIC LIQUID CRYSTAL MIXTURE

[75] Inventors: Ayako Takeichi, Tokorozawa, Japan; Gerhard Illian, Erftstadt, Germany

[73] Assignee: Hoechst Aktiengesellschaft, Frankfurt, Germany

[21] Appl. No.: 822,801

[22] Filed: Mar. 24, 1997

Related U.S. Application Data

[62] Division of Ser. No. 315,091, Sep. 29, 1991, Pat. No. 5,695,683.

[30] Foreign Application Priority Data

Sep. 30, 1993 [JP] Japan ................. 5-245485

[51] Int. Cl.$^6$ ................ C09K 19/34; C09K 19/32
[52] U.S. Cl. ................ 252/299.61; 252/299.62
[58] Field of Search .............. 252/299.61, 299.62

[56] References Cited

U.S. PATENT DOCUMENTS 5,658,492  8/1997  Murashiro et al. ........... 252/299.61

*Primary Examiner*—C. H. Kelly
*Attorney, Agent, or Firm*—Frommer Lawrence & Haug LLP

[57] ABSTRACT

A ferroelectric liquid crystal mixture which does not lower the conventional transition temperature to the ferroelectric phase (60° C. or above), which maintains the Sa phase within a suitable temperature range, and which is useful for reducing the cone angle is disclosed. The ferroelectric liquid crystal mixture contains at least one of the compounds represented by the following general formulae 1 to 3, and exhibits a Sa/Sc phase transition temperature of 60° C. or more and a cone angle of 47 degree or less atsome temperature between 15° C. and 35° C.:

Formula 1:

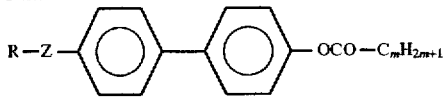

Formula 2:

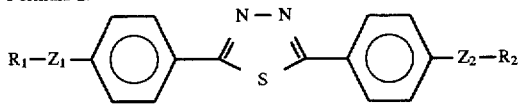

Formula 3:

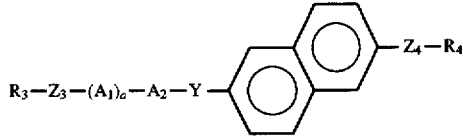

7 Claims, No Drawings

FERROELECTRIC LIQUID CRYSTAL MIXTURE

This application is a division of application Ser. No. 08/315.091. filed Sep. 29, 1994. U.S. Pat. No. 5,695,683.

FIELD OF THE INVENTION

This invention relates to a ferroelectric liquid crystal mixture used for a ferroelectric liquid crystal display device.

In particular in the last decade, liquid crystals have been introduced into various technical areas where electro-optical and display device properties are required (for example in watch, calculator and typewriter displays). These display devices are based on the dielectric alignment effects in the nematic, cholesteric and/or smectic phases of the liquid-crystalline compounds, where, caused by the dielectric anisotropy, the molecular long axes of the compounds adopt a preferred alignment in an applied electric field. The conventional response times in these display devices are too long for many other potential areas of application of liquid crystals. This disadvantage is particularly noticeable if a large number of pixels have to be addressed. The production costs of equipment containing relatively large screen areas are then generally too high.

In addition to nematic and cholesteric liquid crystals, optically active smectic liquid-crystals phases have also been increasing in importance for a few years.

Clark and Lagerwall have been able to show that the use of ferroelekctric liquid-crystal systems in very thin cells give electro-optical switch or display elements which have response times faster by a factor of up to 1000 compared with conventional TN ("twisted nematic") cells (cf., for example, Lagerwall et al., "Ferroelectric Liquid Crystals for Displays", SID Symposium, October Meeting 1985, San Diego, Calif., USA). Due to these and other favorable properties, for example the possibility for bistable switching and the contrast which is virtually independent of the viewing angle, FLCs are fundamentally very suitable for the abovementioned areas of application, for example via matrix adressing. Due to their high contrast and speed, ferroelectric liquid crystals are also particularly suitable in the area of spatial light modulators (cf., for example, U. Efron in "Spatial Light Molulators and Applications", SPIE, Vol. 1150, p. 46 ff).

As described above, a high speed and a high contrast can be achieved with FLC devices as compared with conventional TN type liquid crystal display devices. In the FLC device, values of the speed and the contrast vary reciprocally as described below. More specifically, the contrast is the ratio between the transmission in the bright state and the transmission in the dark state, and the transmission in the bright state depends on the angle between two extinction positions $2\theta_{eff}$ ($\theta_{eff}$ is the effective tilt angle) in accordance with the following equation:

Transmission=$\sin^2(4\theta_{eff})\times\sin^2(\pi d\Delta n/\lambda)$ wherein:
d: cell thickness
$\Delta n$: refraction anisotropy
$\lambda$: wavelength of incident light The switching speed, on the other hand, is determined in accordance with the following equation:

Switching Time=$a\times\sin(\theta_{eff})$ (a:constant)

Some relative values of the switching speed and the contrast calculated by the above equations are shown in Table 1 below:

TABLE 1

Light Transmission in Bright State and Pulse Width
(a relative value to the value at $2\theta_{eff}$ = 45 degree)

| $2\theta_{eff}$ | 55 | 50 | 45 | 40 | 35 | 33 | 30 | 25 | 20 |
|---|---|---|---|---|---|---|---|---|---|
| Transmission | 88 | 97 | 100 | 97 | 88 | 83 | 75 | 59 | 41 |
| Pulse Width (Switching Time) | 120 | 110 | 100 | 89 | 79 | 74 | 68 | 56 | 45 |

According to Table 1, the contrast reaches its maximum value when the angle between the two extinction positions $2\theta_{eff}$ is 45 degree, and the speed increases as $2\theta_{eff}$ approaches 0 degree. As set forth above, in the range of $2\theta_{eff}$ <45 degree, achievement of both a high transmission and a high speed is apparently contradictory. For this reason, when the liquid crystal cell is used as a display device, these properties must be optimized.

For example, a liquid crystal mixture having $2\theta_{eff}$ of 33 degree has a transmission of only 80%, as compared with that of 45 degree, the switching speed, however, is improved by 26%.

In recent years, a study has been made with respect increasing both the effective angle $2\theta_{eff}$ and the cone angle which is twice the angle between a phase normal of the smectic phase and the director of the molecule (i.e., an average direction of long axis of the molecule). This can be achieved by the electric field treatment of the chevron oriented cell or by using an alignment layer inducing a high pretilt angle. In order to achieve the speed and the contrast suitable for the display device in the above-described modes, a liquid crystal mixture having a $2\theta_{eff}$ of from 28 to 45 degree is required. Alternatively, since the effective angle is generally smaller than the cone angle by about 2 degree, the cone angle is required to be 30 to 47 degree.

Conventional liquid crystal mixtures mainly contain compounds such as phenylpyrimidines, phenyl benzoates, phenylpyridines, pyridylpyrimidines, difluorophenylpyrimidines, phenylfluoropyridines and diphenylpyrimidines. These compounds are disclosed in examples of the prior art, for example, European Patent Publication Nos. 0284008, 0308794, 0307880, 0318423, 0288813 and 0451821, and International Publication Nos. 90/11547, 90/11336 and 91/08272. In these liquid crystal mixtures, $2\theta_{eff}$ is about 45 degree and about 55 degree at Sc/Sa phase transition temperatures of 60° C. and 70° C., respectively.

In order to achieve the above-described suitable switching speed and contrast, it is necessary to reduce the cone angle of the liquid crystal mixture. The cone angle is generally easily reduced by lowering the phase transition temperature. However, since an operable temperature range of the liquid crystal material becomes narrow as the phase transition temperature lowers, an application of the liquid crystal material having a low phase transition temperature to a display device is not practical. For applying it to the display device, it is required that the liquid crystal material generally has a ferroelectric phase at a temperature of 60° C. or above in order to ensure the operable temperature range of the liquid crystal material. Also, the cone angle is reduced by adding a large amount of compounds having a broad Sa phase to the liquid crystal mixture (Atsuo Fukuta et al., "Structure and Physical Properties of Ferroelectric Liquid Crystal", Corona Co.).

However, this method has a disadvantage in that, since a transition point to the isotropic phase exceeds 100° C., the cell must be filled with the liquid crystal at a high temperature, and thus materials which constitute the cell are restricted.

Accordingly, the object of the present invention is to provide a liquid crystal 30 mixture which does not lower the conventional transition temperature to the ferroelectric phase (60° C. or above), which maintains the Sa phase at a suitable temperature range, and which is useful for reducing the cone angle.

DETAILED DESCRIPTION OF THE INVENTION

The ferroelectric liquid crystal mixture according to the present invention comprises at least one of the compounds represented by the following general formulae 1, 2 and 3. and having a Sc/Sa phase transition temperature of 60° C. or above and a cone angle of 47 degree or less at some temperature between 15° C. and 35° C.:

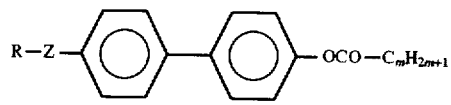

Formula 1:

wherein one or more hydrogen atoms of the aromatic ring may be substituted with a substituent selected from the group consisting of F, Cl and CN;

m is an integer of from 1 to 16;

R represents (a) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or

(b):

wherein n is an integer of from 1 to 10; and

Z is a single bond, —O—, —CO—O—, —O—CO—, —O—$CH_2$ or —$CH_2$O—; provided that, when R is (b), Z is —CO—O— or —$CH_2$—O—

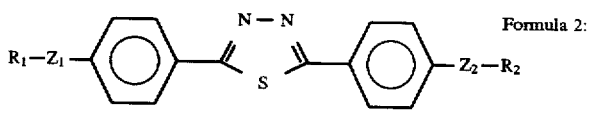

Formula 2:

wherein at least one optional=C-H group of the aromatic ring may be substituted with =C-F or =N-;

$R_1$ and $R_2$ each independently represents (a) a hydrogen atom;

(b) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or

(c):

wherein n is an Integer of from 1 to 10; and $Z_1$ and $Z_2$ each represents a single bond, —O—, —CO—O—, —O—CO—, —O—$CH_2$— or —$CH_2$O—; provided that, when $R_1$ is (c), $Z_1$ is —CO—O—or —$CH_2$—O—and that, when $R_2$ is (c), $Z_2$ is —O—CO—or —O—$CH_2$—;

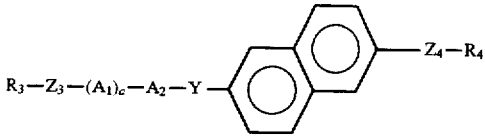

Formula 3:

wherein $A_1$ and $A_2$, which may be the same or different, each represents 1,4-phenylene in which one or two hydrogen atoms may be substituted with a substituent selected from the group consisting of F, Cl and CN, or pyrazine-2,5-diyl, pyridazine-3,6-diyl, pyridine-2,5-diyl or pyrimidine-2,5-diyl in which one or two hydrogen atoms may be substituted with F;

a Is 0 or 1;

$R_3$ and $R_4$ each Independently represents (a) a hydrogen atom;

(b) a straight chain or branched chain alkyl group having from 2 to 16 carbon atoms, in which one or two non-adjacent —$CH_2$— groups may be substituted with —O—, —S—, —CO—, —CO—O—, —O—CO—, —CO—S—, —S—CO—, —CH=CH—, —C≡C—, —Si($CH_3$)$_2$—, a chiral epoxy group or —O—CO—O—; one or more hydrogen atoms of the alkyl group may be substituted with a substituent selected from the group consisting of F, Cl and CN; and a terminal methyl group may be substituted with a cyclopropyl group or a cyclohexyl group; or

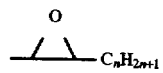

(c):

wherein n is an integer of from 1 to 10; Y is a single bond, —O—CO—, —CO—O—, —O—$CH_2$— or —$CH_2$—O— or Y is a single bond or —O—CO—; and $Z_3$ and $Z_4$ each represents a single bond, —O—, —CO—O—, —O—CO—, —$CH_2$—O— or —O—$CH_2$; provided that, when $R_3$ is (c), $Z_3$ is —CO—O— or —$CH_2$—O and that, when $R_4$ is (c), $Z_4$ is —O—CO— or —O—$CH_2$.

Preferably, the ferroelectric liquid crystal mixture according to the present invention comprises at least one of the liquid crystal compounds represented by the following general formulae 1, 2 and 3:

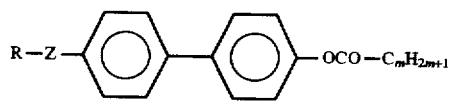

Formula 1:

wherein m is an integer of from 1 to 16;

R represents a straight chain or branched chain alkyl group having from 2 to 16 carbon atoms, in which one or two non-adjacent —$CH_2$— groups may be substituted with —O—, —CO—, —CO—O—, —O—CO— or —O—CO—O—, and a terminal methyl group may be substituted with a cyclopropyl group or a cyclohexyl group; and Z is a single bond, —O—, —CO—O—, —O—CO—, —CH$_2$—O— or —O—CH$_2$—;

Formula 2:

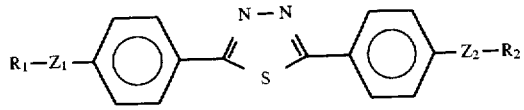

wherein at least one optional =C-H group of the aromatic ring may be substituted with =C-F or =N—;

R$_1$ and R$_2$ each independently represents
  (a) a hydrogen atom;
  (b) a straight chain or branched chain alkyl group having from 2 to 16 carbon atoms, in which one or two non-adjacent —CH$_2$— groups may be substituted with —O—, —CO—O—, —O—CO—, —Si(CH$_3$)$_2$—, a chiral epoxy group or —O—CO—O—, and a terminal methyl group may be substituted with a cyclopropyl group or a cyclohexyl group; or (c):

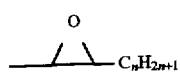

wherein n is an integer of from 1 to 10; and Z$_1$ and Z$_2$ each represents a single bond, —O—, —CO—O—, —O—CO—, —O—CH$_2$— or —CH$_2$—O—; provided that, when R$_1$ is (c), Z$_1$ is —CO—O— or —CH$_2$—O— and that, when R$_2$ is (c), Z$_2$ is —O—CO— or —O—CH$_2$—

Formula 3:

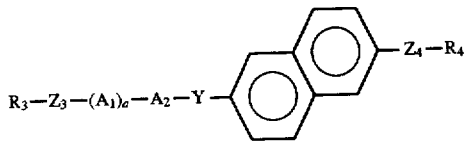

wherein A$_1$ and A$_2$, which may be the same or different, each represents 1,4-phenylene, pyridine-2,5-diyl or pyrimidine-2,5-diyl in which one or two hydrogen atoms may be substituted with F;

a is 0 or 1;

R$_3$ and R$_4$ each independently represents
  (a) a hydrogen atom;
  (b) a straight chain or branched chain alkyl group having from 2 to 16 carbon atoms, in which one or two non-adjacent —CH$_2$— groups may be substituted with —O—, —CO—, —CO—O—, —O—CO—, —Si(CH$_3$)$_2$—, a chiral epoxy group or —O—CO—O—; and a terminal methyl group may be substituted with a cyclopropyl group or a cyclohexyl group; or (c):

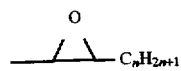

wherein n is an integer of from 1 to 10; —O—CO—, —CO—O—, —O—CH$_2$— or —CH$_2$—O—or Y is a single bond or —O—CO— and Z$_3$ and Z$_4$ each represents a single bond, —O—, —CO—O—, —O—CO—, —O—CH$_2$— or —CH$_2$—O—; provided that, when R$_3$ is (c), Z$_3$ is —CO—O— or —CH$_2$—O— and that, when R$_4$ is (c), Z$_4$ is —O—CO— or —O—CH$_2$—.

Ferroelectric liquid crystal mixtures according to the invention have a S$_C$-S$_A$ phase transition temperature of 60° C. or more and a cone angle of 47° or less at some temperature between 15° C. and 35° C., preferably between 20° C. and 30° C., more preferably between 20° C. and 25° C.

When any of the compounds represented by the general formulae 1 to 3 above is contained in the liquid crystal mixture in an amount of preferably 5% or more, and more preferably from 10 to 50%, the transition temperature to the ferroelectric phase can be maintained at 60° C. or more, the Sa phase can be maintained in the appropriate temperature range, and the cone angle can be reduced.

Of the compounds represented by the general formula 1, preferred compounds include the compounds represented by the following general formula (1a):

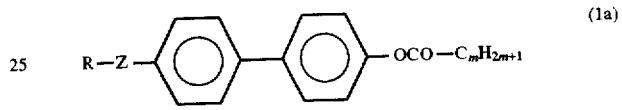

wherein m is an integer of from 1 to 16; R represents a straight chain or branched chain alkyl group having from 2 to 16 carbon atoms, in which one or two non-adjacent —CH$_2$— groups may be substituted with —O—, —CO—, —CO—O—, —O—CO—, or —O—CO—O—, and a terminal methyl group may be substituted with a cyclopropyl group or a cyclohexyl group; and Z is a single bond, —O—, —CO—O—or —O—CO—. More preferably, Z in the formula (1a) represents —O— or —CO—O—.

Further, in the compounds represented by the general formula 1, R is preferably an n-alkyl group having from 1 to 16 carbon atoms.

Particularly preferred compounds represented by the general formula 1 include the following compounds.

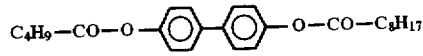
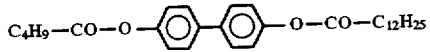
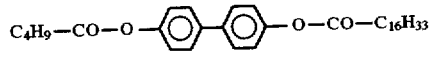
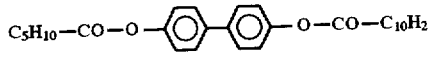
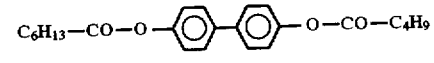
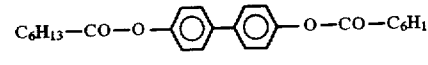
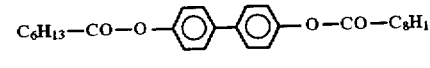
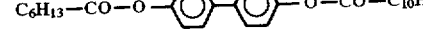
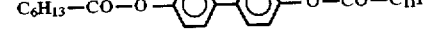

-continued

C₆H₁₃—CO—O—⟨⟩—⟨⟩—O—CO—C₁₂H₂₅

C₆H₁₃—CO—O—⟨⟩—⟨⟩—O—CO—C₁₄H₂₉

C₇H₁₅—CO—O—⟨⟩—⟨⟩—O—CO—C₅H₁₁

C₇H₁₅—CO—O—⟨⟩—⟨⟩—O—CO—C₆H₁₃

C₇H₁₅—CO—O—⟨⟩—⟨⟩—O—CO—C₇H₁₅

C₈H₁₇—CO—O—⟨⟩—⟨⟩—O—CO—C₄H₉

C₈H₁₇—CO—O—⟨⟩—⟨⟩—O—CO—C₆H₁₃

C₈H₁₇—CO—O—⟨⟩—⟨⟩—O—CO—C₇H₁₅

C₈H₁₇—CO—O—⟨⟩—⟨⟩—O—CO—C₈H₁₇

C₈H₁₇—CO—O—⟨⟩—⟨⟩—O—CO—C₉H₁₉

C₈H₁₇—CO—O—⟨⟩—⟨⟩—O—CO—C₁₀H₂₁

C₈H₁₇—CO—O—⟨⟩—⟨⟩—O—CO—C₁₂H₂₅

C₉H₁₉—CO—O—⟨⟩—⟨⟩—O—CO—C₅H₁₁

C₉H₁₉—CO—O—⟨⟩—⟨⟩—O—CO—C₆H₁₃

C₉H₁₉—CO—O—⟨⟩—⟨⟩—O—CO—C₈H₁₇

C₉H₁₉—CO—O—⟨⟩—⟨⟩—O—CO—C₉H₁₉

C₉H₁₉—CO—O—⟨⟩—⟨⟩—O—CO—C₁₀H₂₁

C₁₀H₂₁—CO—O—⟨⟩—⟨⟩—O—CO—C₃H₇

C₁₀H₂₁—CO—O—⟨⟩—⟨⟩—O—CO—C₄H₉

C₁₀H₂₁—CO—O—⟨⟩—⟨⟩—O—CO—C₅H₁₁

C₁₀H₂₁—CO—O—⟨⟩—⟨⟩—O—CO—C₆H₁₃

C₁₀H₂₁—CO—O—⟨⟩—⟨⟩—O—CO—C₇H₁₅

C₁₀H₂₁—CO—O—⟨⟩—⟨⟩—O—CO—C₈H₁₇

C₁₀H₂₁—CO—O—⟨⟩—⟨⟩—O—CO—C₉H₁₉

C₁₀H₂₁—CO—O—⟨⟩—⟨⟩—O—CO—C₁₀H₂₁

-continued

C₁₀H₂₁—CO—O—⟨⟩—⟨⟩—O—CO—C₁₁H₂₃

C₁₁H₂₃—CO—O—⟨⟩—⟨⟩—O—CO—C₄H₉

C₁₁H₂₃—CO—O—⟨⟩—⟨⟩—O—CO—C₅H₁₁

C₁₁H₂₃—CO—O—⟨⟩—⟨⟩—O—CO—C₆H₁₃

C₁₁H₂₃—CO—O—⟨⟩—⟨⟩—O—CO—C₇H₁₅

C₁₁H₂₃—CO—O—⟨⟩—⟨⟩—O—CO—C₈H₁₇

C₁₁H₂₃—CO—O—⟨⟩—⟨⟩—O—CO—C₉H₁₉

C₁₁H₂₃—CO—O—⟨⟩—⟨⟩—O—CO—C₁₀H₂₁

C₁₂H₂₅—CO—O—⟨⟩—⟨⟩—O—CO—C₂H₅

C₁₂H₂₅—CO—O—⟨⟩—⟨⟩—O—CO—C₄H₉

C₁₂H₂₅—CO—O—⟨⟩—⟨⟩—O—CO—C₆H₁₃

C₁₂H₂₅—CO—O—⟨⟩—⟨⟩—O—CO—C₈H₁₇

C₁₄H₂₉—CO—O—⟨⟩—⟨⟩—O—CO—C₅H₁₁

C₄H₉—CO—O—⟨⟩—⟨⟩—O—CO—▷

C₅H₁₁—CO—O—⟨⟩—⟨⟩—O—CO—▷

C₆H₁₃—CO—O—⟨⟩—⟨⟩—O—CO—▷

C₇H₁₅—CO—O—⟨⟩—⟨⟩—O—CO—▷

C₈H₁₇—CO—O—⟨⟩—⟨⟩—O—CO—▷

C₉H₁₉—CO—O—⟨⟩—⟨⟩—O—CO—▷

C₁₀H₂₁—CO—O—⟨⟩—⟨⟩—O—CO—▷

C₁₁H₂₃—CO—O—⟨⟩—⟨⟩—O—CO—▷

C₁₂H₂₅—CO—O—⟨⟩—⟨⟩—O—CO—▷

C₁₃H₂₇—CO—O—⟨⟩—⟨⟩—O—CO—▷

C₁₄H₂₉—CO—O—⟨⟩—⟨⟩—O—CO—▷

-continued $C_4H_9-CO-O-\langle\text{Ph}\rangle-\langle\text{Ph}\rangle-O-CH_2-\triangleleft$ $C_5H_{11}-CO-O-\langle\text{Ph}\rangle-\langle\text{Ph}\rangle-O-CH_2-\triangleleft$ $C_6H_{13}-CO-O-\langle\text{Ph}\rangle-\langle\text{Ph}\rangle-O-CH_2-\triangleleft$ $C_7H_{15}-CO-O-\langle\text{Ph}\rangle-\langle\text{Ph}\rangle-O-CH_2-\triangleleft$ $C_8H_{17}-CO-O-\langle\text{Ph}\rangle-\langle\text{Ph}\rangle-O-CH_2-\triangleleft$ $C_9H_{19}-CO-O-\langle\text{Ph}\rangle-\langle\text{Ph}\rangle-O-CH_2-\triangleleft$ $C_{10}H_{21}-CO-O-\langle\text{Ph}\rangle-\langle\text{Ph}\rangle-O-CH_2-\triangleleft$ $C_{11}H_{23}-CO-O-\langle\text{Ph}\rangle-\langle\text{Ph}\rangle-O-CH_2-\triangleleft$ $C_{12}H_{25}-CO-O-\langle\text{Ph}\rangle-\langle\text{Ph}\rangle-O-CH_2-\triangleleft$ $C_{13}H_{27}-CO-O-\langle\text{Ph}\rangle-\langle\text{Ph}\rangle-O-CH_2-\triangleleft$ $C_{14}H_{29}-CO-O-\langle\text{Ph}\rangle-\langle\text{Ph}\rangle-O-CH_2-\triangleleft$ $C_3H_7-\underset{(R)}{C}\overset{O}{-}\underset{(R)}{C}-CO-O-\langle\text{Ph}\rangle-\langle\text{Ph}\rangle-O-CO-C_4H_9$ $C_3H_7-\underset{(R)}{C}\overset{O}{-}\underset{(R)}{C}-CO-O-\langle\text{Ph}\rangle-\langle\text{Ph}\rangle-O-CO-C_5H_{11}$ $C_3H_7-\underset{(R)}{C}\overset{O}{-}\underset{(R)}{C}-CO-O-\langle\text{Ph}\rangle-\langle\text{Ph}\rangle-O-CO-C_6H_{13}$ $C_3H_7-\underset{(R)}{C}\overset{O}{-}\underset{(R)}{C}-CO-O-\langle\text{Ph}\rangle-\langle\text{Ph}\rangle-O-CO-C_7H_{15}$ $C_3H_7-\underset{(R)}{C}\overset{O}{-}\underset{(R)}{C}-CO-O-\langle\text{Ph}\rangle-\langle\text{Ph}\rangle-O-CO-C_8H_{17}$ $C_3H_7-\underset{(R)}{C}\overset{O}{-}\underset{(R)}{C}-CO-O-\langle\text{Ph}\rangle-\langle\text{Ph}\rangle-O-CO-C_9H_{19}$ $C_3H_7-\underset{(R)}{C}\overset{O}{-}\underset{(R)}{C}-CO-O-\langle\text{Ph}\rangle-\langle\text{Ph}\rangle-O-CO-C_{10}H_{21}$ $C_3H_7-\underset{(R)}{C}\overset{O}{-}\underset{(R)}{C}-CO-O-\langle\text{Ph}\rangle-\langle\text{Ph}\rangle-O-CO-C_{11}H_{23}$ $C_3H_7-\underset{(R)}{C}\overset{O}{-}\underset{(R)}{C}-CO-O-\langle\text{Ph}\rangle-\langle\text{Ph}\rangle-O-CO-C_{12}H_{25}$ -continued $C_3H_7-\underset{(R)}{C}\overset{O}{-}\underset{(R)}{C}-CO-O-\langle\text{Ph}\rangle-\langle\text{Ph}\rangle-O-CO-C_{13}H_{27}$ $C_3H_7-\underset{(R)}{C}\overset{O}{-}\underset{(R)}{C}-CO-O-\langle\text{Ph}\rangle-\langle\text{Ph}\rangle-O-CO-C_{14}H_{29}$ $C_4H_9-\underset{(S)}{C}\overset{O}{-}\underset{(S)}{C}-CH_2-O-\langle\text{Ph}\rangle-\langle\text{Ph}\rangle-O-CO-C_4H_9$ $C_4H_9-\underset{(S)}{C}\overset{O}{-}\underset{(S)}{C}-CH_2-O-\langle\text{Ph}\rangle-\langle\text{Ph}\rangle-O-CO-C_5H_{11}$ $C_4H_9-\underset{(S)}{C}\overset{O}{-}\underset{(S)}{C}-CH_2-O-\langle\text{Ph}\rangle-\langle\text{Ph}\rangle-O-CO-C_6H_{13}$ $C_4H_9-\underset{(S)}{C}\overset{O}{-}\underset{(S)}{C}-CH_2-O-\langle\text{Ph}\rangle-\langle\text{Ph}\rangle-O-CO-C_7H_{15}$ $C_4H_9-\underset{(S)}{C}\overset{O}{-}\underset{(S)}{C}-CH_2-O-\langle\text{Ph}\rangle-\langle\text{Ph}\rangle-O-CO-C_8H_{17}$ $C_4H_9-\underset{(S)}{C}\overset{O}{-}\underset{(S)}{C}-CH_2-O-\langle\text{Ph}\rangle-\langle\text{Ph}\rangle-O-CO-C_9H_{19}$ $C_4H_9-\underset{(S)}{C}\overset{O}{-}\underset{(S)}{C}-CH_2-O-\langle\text{Ph}\rangle-\langle\text{Ph}\rangle-O-CO-C_{10}H_{21}$ $C_4H_9-\underset{(S)}{C}\overset{O}{-}\underset{(S)}{C}-CH_2-O-\langle\text{Ph}\rangle-\langle\text{Ph}\rangle-O-CO-C_{11}H_{23}$ $C_4H_9-\underset{(S)}{C}\overset{O}{-}\underset{(S)}{C}-CH_2-O-\langle\text{Ph}\rangle-\langle\text{Ph}\rangle-O-CO-C_{12}H_{25}$ $C_4H_9-\underset{(S)}{C}\overset{O}{-}\underset{(S)}{C}-CH_2-O-\langle\text{Ph}\rangle-\langle\text{Ph}\rangle-O-CO-C_{13}H_{27}$ $C_4H_9-\underset{(S)}{C}\overset{O}{-}\underset{(S)}{C}-CH_2-O-\langle\text{Ph}\rangle-\langle\text{Ph}\rangle-O-CO-C_{14}H_{29}$ $C_8H_{17}-O-\langle\text{Ph}\rangle-\langle\text{Ph}\rangle-O-CO-C_5H_{11}$ $C_8H_{17}-O-\langle\text{Ph}\rangle-\langle\text{Ph}\rangle-O-CO-C_6H_{13}$ $C_{10}H_{21}-O-\langle\text{Ph}\rangle-\langle\text{Ph}\rangle-O-CO-C_5H_{11}$ $C_{10}H_{21}-O-\langle\text{Ph}\rangle-\langle\text{Ph}\rangle-O-CO-C_7H_{15}$ $C_{10}H_{21}-O-\langle\text{Ph}\rangle-\langle\text{Ph}\rangle-O-CO-C_8H_{17}$ Of the compounds represented by the general formula 2, preferred compounds include the compounds represented by the following general formulae (2a), (2b), (2c) and (2d):

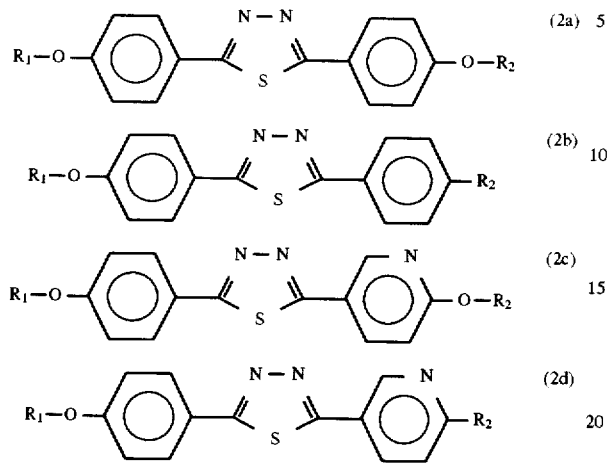

wherein $R_1$ is preferably an n-alkyl group having from 1 to 16 carbon atoms, and $R_2$ is preferably selected from the groups represented by the following formulae (2-i) to (2-v):

(2-i) an n-alkyl group having from 1 to 16 carbon atoms;

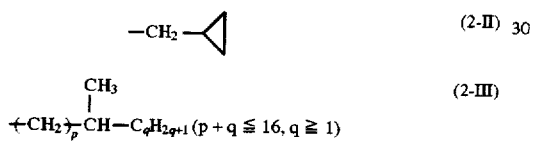

(2-iv) a cyclohexyl group; and (2-v) H.

Further, in the compounds represented by the formulae (2a), (2b) and (2c), $R_1$ and $R_2$ are preferably an n-alkyl group having from 1 to 16 carbon atoms.

Particularly preferred compounds represented by the general formula 2 include the following compounds.

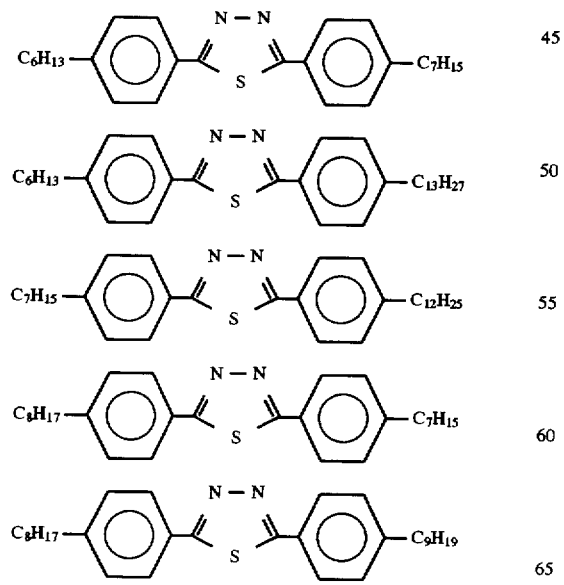

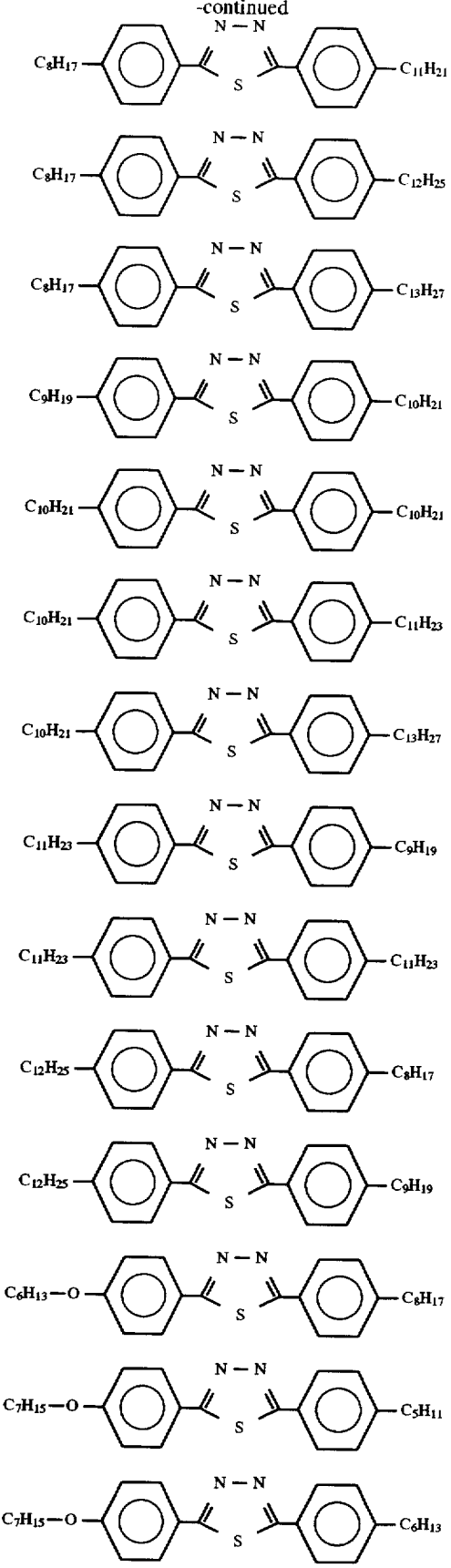

-continued
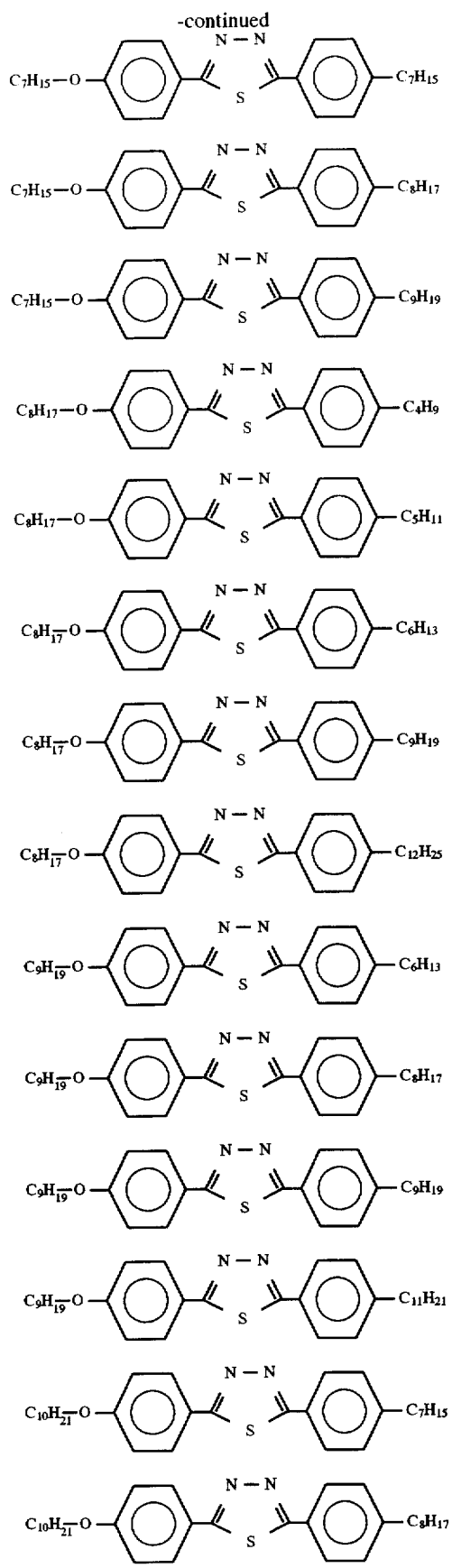
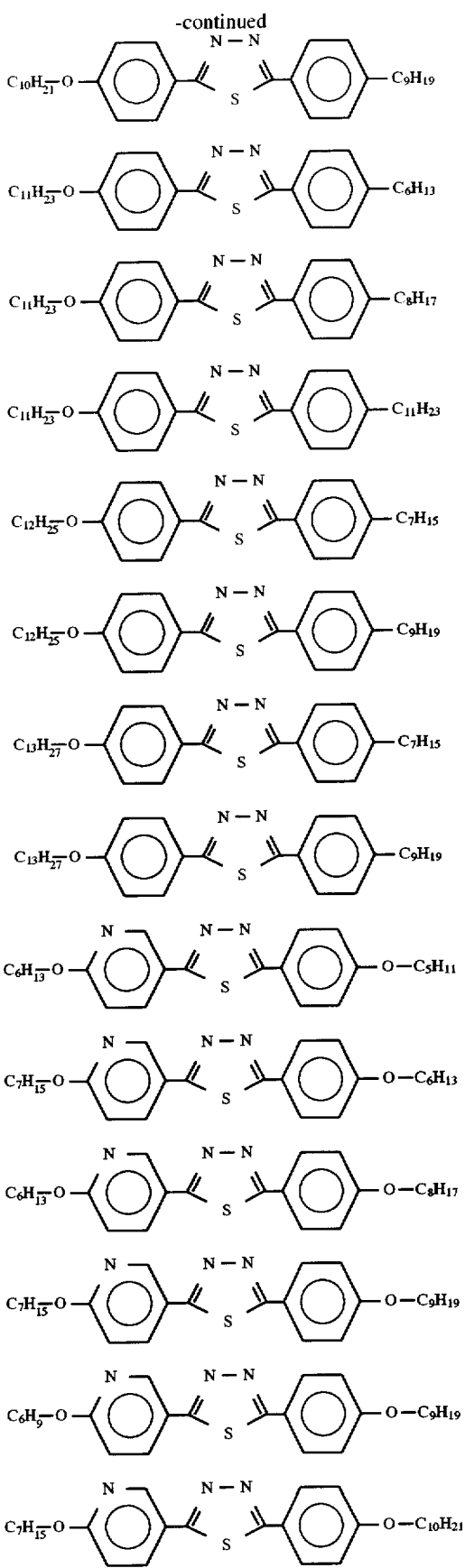

-continued

-continued
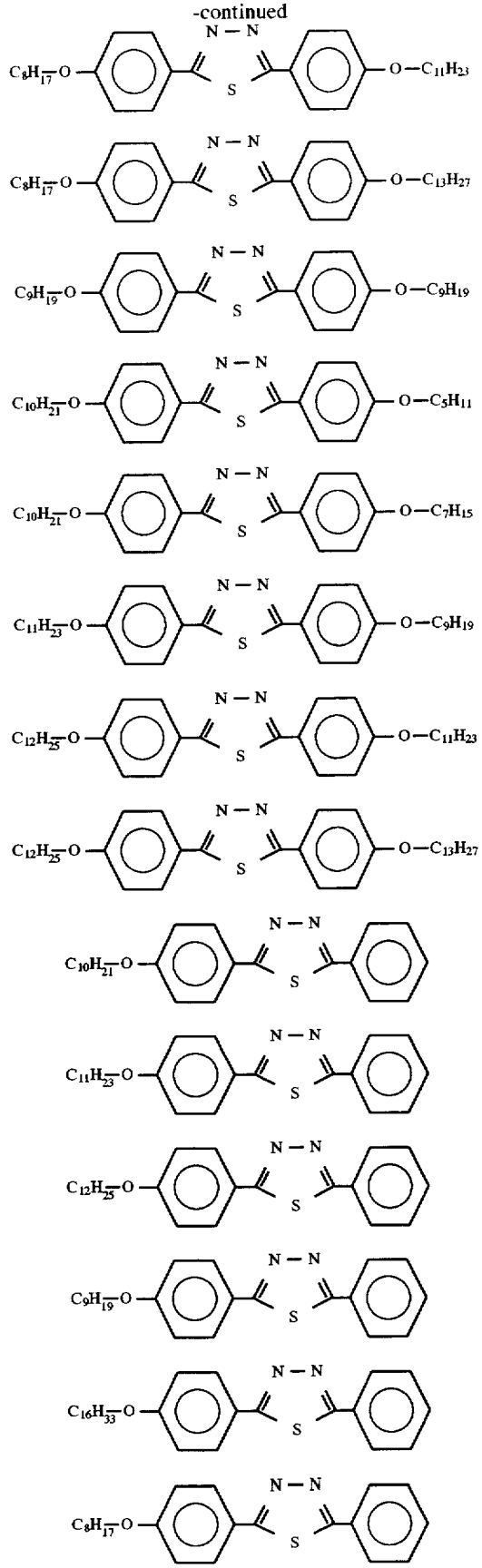
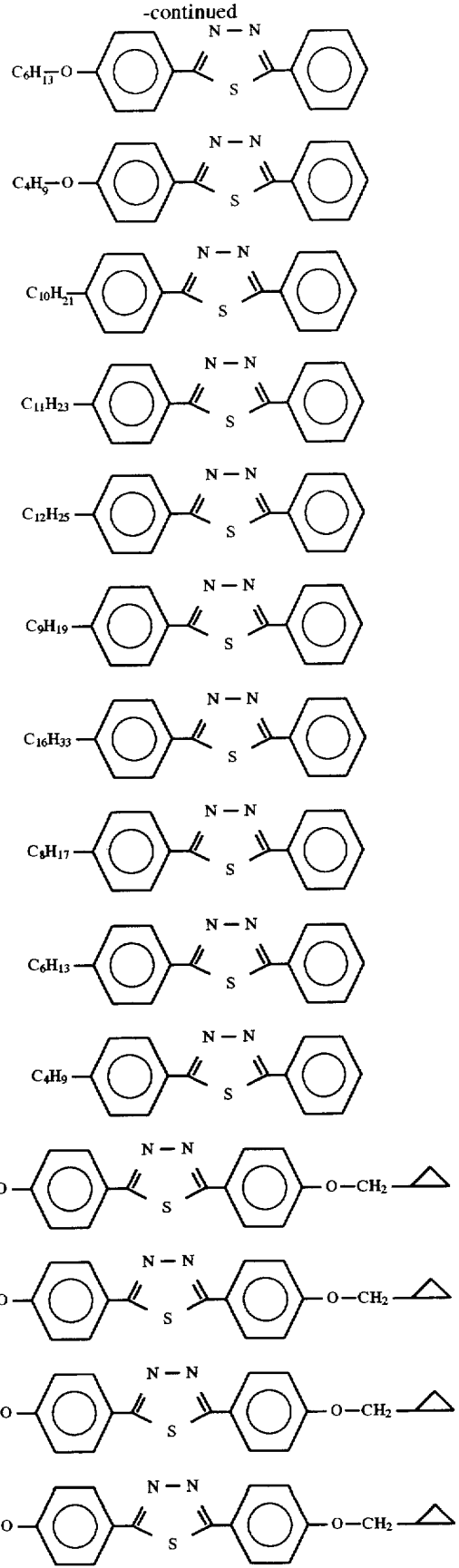

-continued

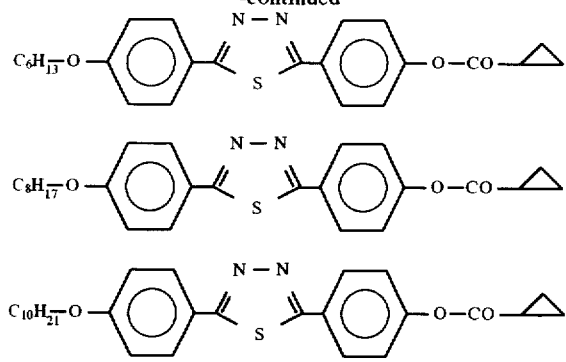

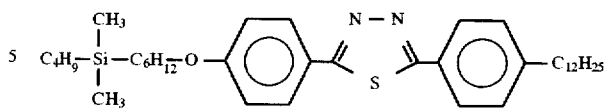

Of the compounds represented by the general formula 3, preferred compounds include the compounds represented by the following general formulae (3a) and (3b):

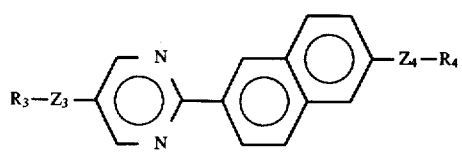
(3a)

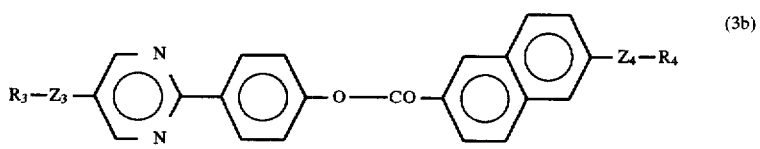
(3b)

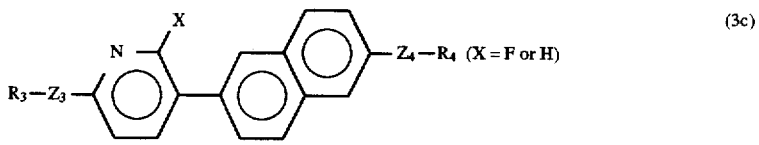
(3c)

(X = F or H)

-continued

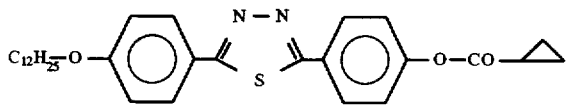

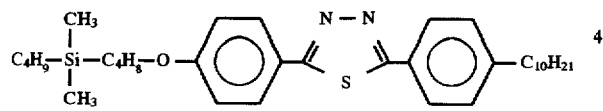

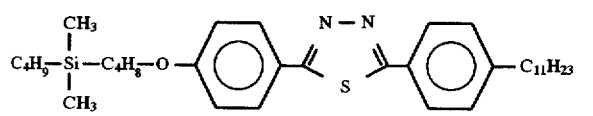

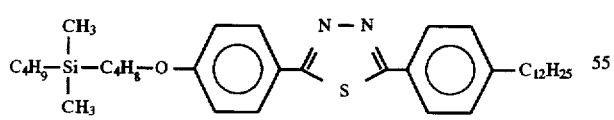

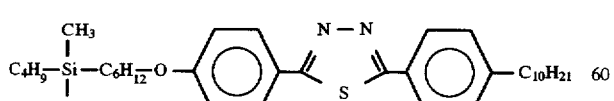

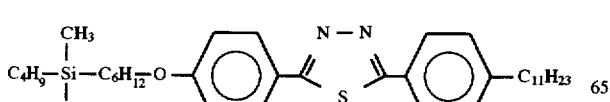

wherein $R_3$ and $R_4$ are preferably a group selected from the groups represented by the following formulae (3-i) and (3-ii):

(3-i) an n-alkyl group having from 1 to 16 carbon atoms;

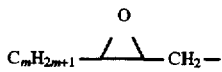

wherein m is an integer of from 1 to 16.

Further, In the compounds represented by the formulae 3, $Z_3$ and $Z_4$ are preferably —O—.

Particularly preferred compounds represented by the general formula 3 include the following compounds.

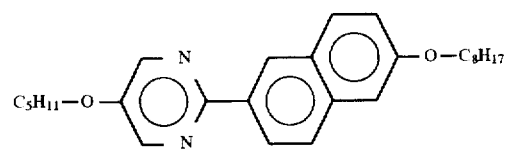
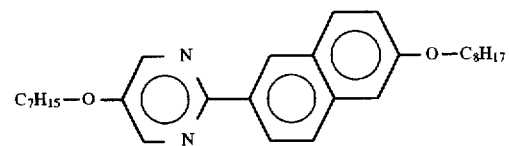
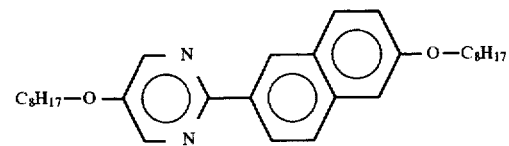
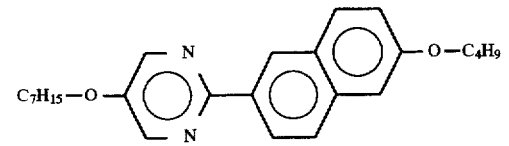
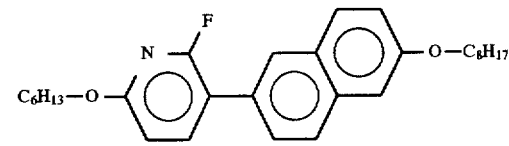
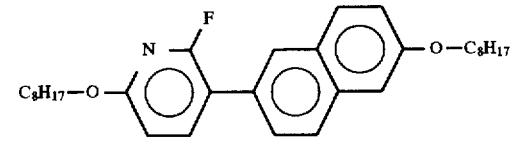
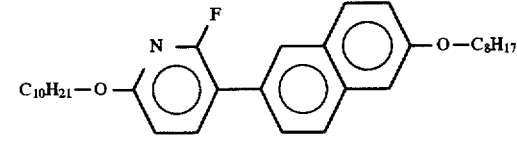
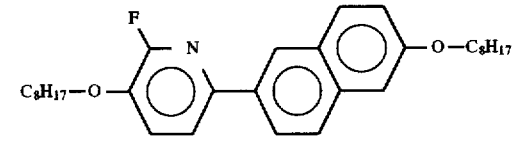
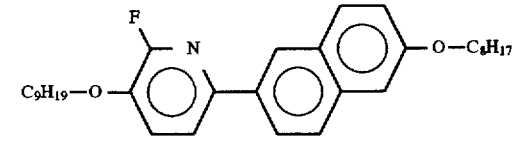
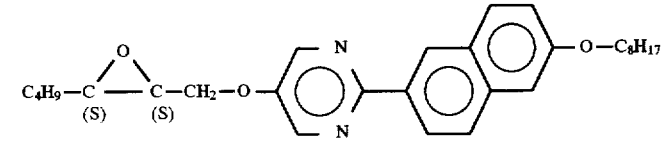
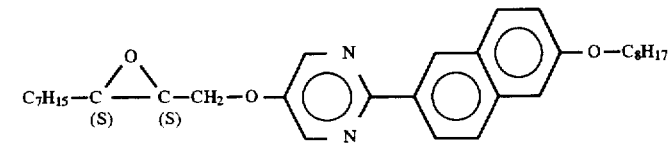

-continued

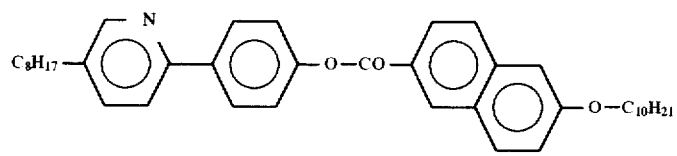

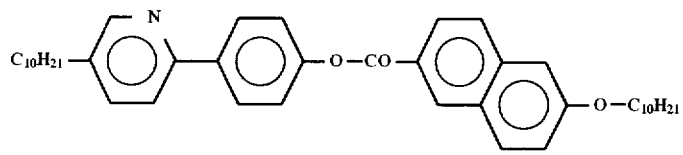

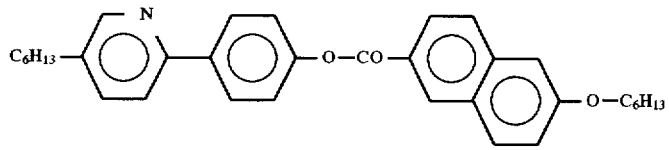

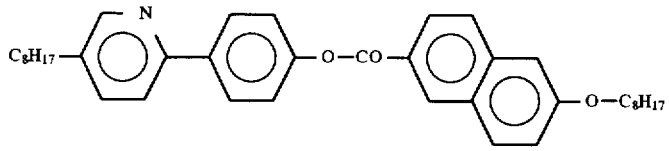

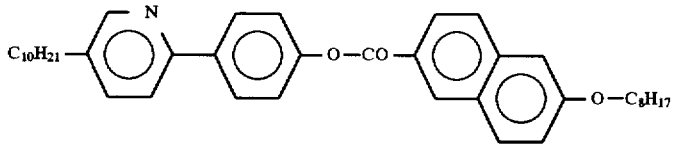

The ferroelectric liquid crystal mixture of the present invention comprises at least one of the compounds of the general formulae 1, 2 or 3. Preferably It comprises at least one compound of the formula 1. More preferably It comprises at least one compound of each of the formulae 1 and 2 or 1 and 3 or 2 and 3. In particular it comprises at least one compound of each of the formulae 1, 2 and 3. By using these compounds in combination, a smaller cone angle can be obtained, and the miscibility in the liquid crystal mixture can be improved so that the melting point of the FLC mixture can be lowered.

The content of each of the compounds of the general formulae 1 to 3 in the liquid crystal mixture is preferably from 5% to 50%, more preferably from 10% to 50% (all percentages are by weight). Also, the mixture according to the present invention may contain phenylpyridine at a concentration of from 10% to 50% together with the compounds of the general formulae 1 to 3.

The present invention is further Illustrated in more detail by the following examples.

The general procedure for determining the effective angle and the one angle is as follows:

The mixture is filled Into a test cell having a thickness of 2 μm and subjected to field treatment by applying a rectangular pulse of 30 V at 10 Hz for 30 seconds.

To determine the effective angle and the cone angle the measuring cell is mounted on the revolving stage of a polarizing microscope between crossed analyser and polarizer.

By rotating the stage, the position of the stage with minimum light transmission is determined for the two switching states in the cell. The difference between the two positions on the revolving stage is equal to the effective angle if the switching field is turned off and is equal to the cone angle if the switching field is applied during the measurement.

In all examples the determination of the cone angle is made at a temperature 40° C. below the $S_C$-$S_A$ phase transition temperature of the mixture.

EXAMPLE 1

The following compounds were mixed at the indicated weight ratio (%) to prepare a liquid crystal mixture A.

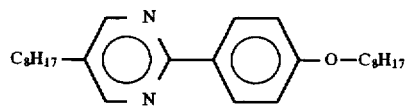 12

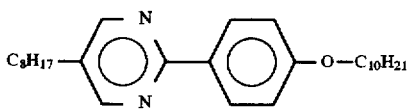 10

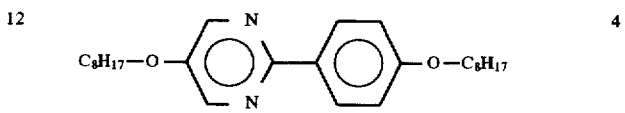 4

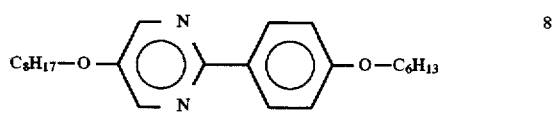 8

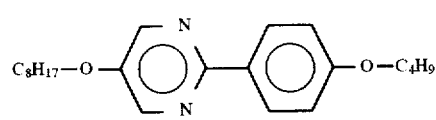
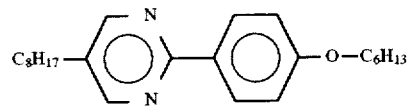
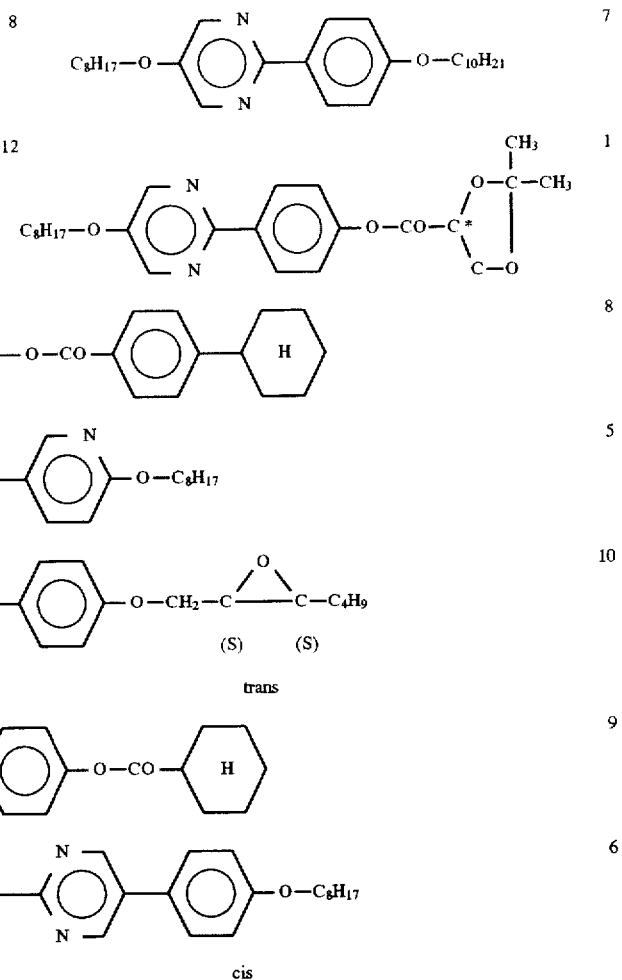

Then, the following compounds were mixed with the above-prepared liquid crystal mixture A at the indicated weight ratio (%) to prepare a liquid crystal mixture B.

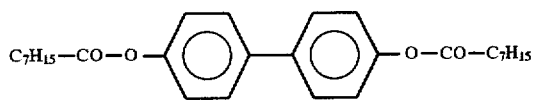
3

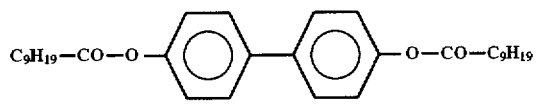
3

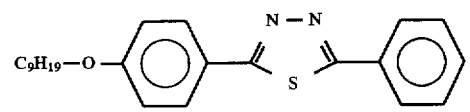
3

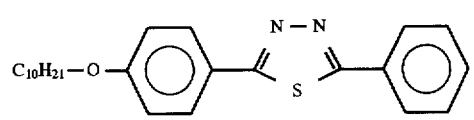
3

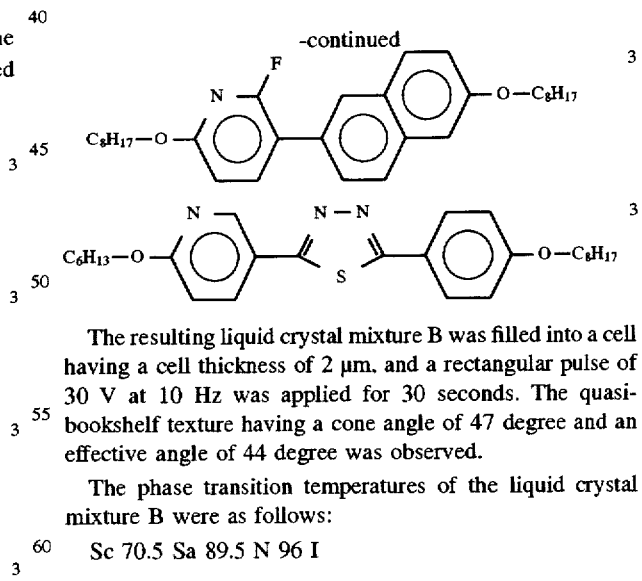

The resulting liquid crystal mixture B was filled into a cell having a cell thickness of 2 μm, and a rectangular pulse of 30 V at 10 Hz was applied for 30 seconds. The quasi-bookshelf texture having a cone angle of 47 degree and an effective angle of 44 degree was observed.

The phase transition temperatures of the liquid crystal mixture B were as follows:

Sc 70.5 Sa 89.5 N 96 I

Comparative Example 1

In the same manner as described in Example 1, the liquid crystal mixture A was filled Into the cell having a cell thickness of 2 μm, and a rectangular pulse of 30 V at 10 Hz was applied for 30 seconds. As a result, the quasi-bookshelf texture having a cone angle of 50 degree and an effective angle of 48 was observed.

The phase transition temperatures of the liquid crystal mixture A were as follows:

Sc 69 Sa 86.5 N 93 I

The liquid crystal mixture A comprises typical phenylpyrimidines, and, as compared with the liquid crystal mixture B, the cone angle is higher than that of the mixture B by 3 degree, while the Sc/Sa phase transition temperature is lower than that of the mixture B by 1.5 degree. Also, the effective angle is as high as 45 degree, and the transmission shown by the liquid crystal mixture is slightly low. This indicates that the compounds according to the present invention are very useful for improving the transmission and speed by reducing the cone angle of the conventional phenylpyrimidine liquid crystal mixtures.

EXAMPLE 2

The following compounds were mixed at the indicated weight ratio (%) to prepare a liquid crystal mixture C.

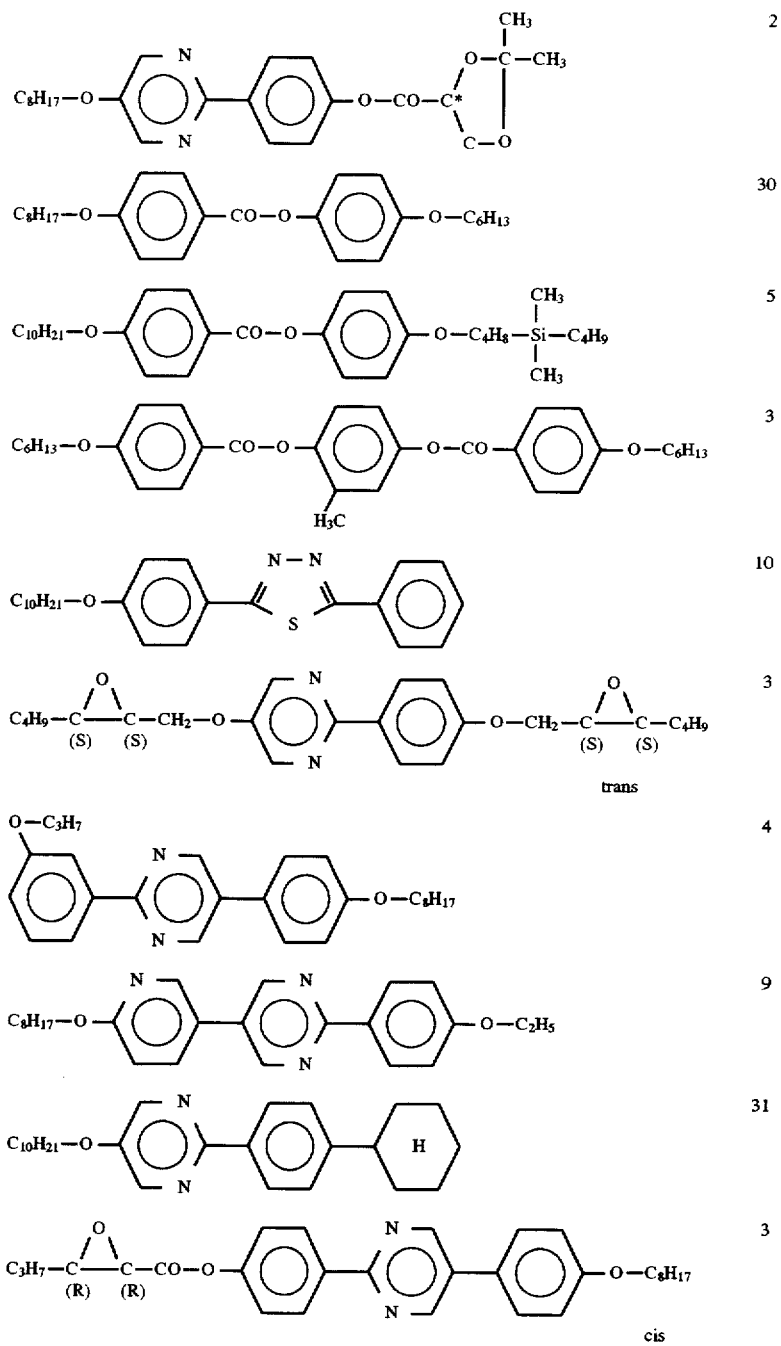

Then, the following compounds were mixed with the above-prepared liquid crystal mixture C at the indicated weight ratio (%) to prepare a liquid crystal mixture D.

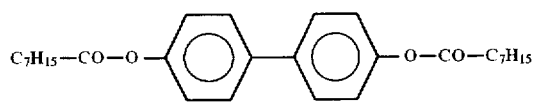 6

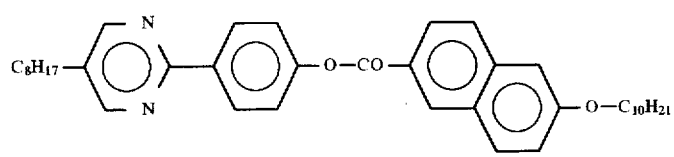 7

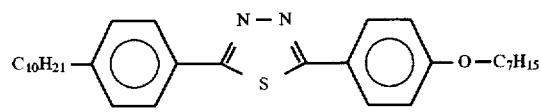 6

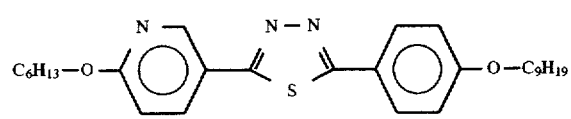 3

The resulting liquid crystal mixture D was filled Into a cell having a cell thickness of 2 pm, and a rectangular pulse of 30 V at 1 OHz was applied for 30 seconds. The quasi-bookshelf texture having a cone angle of 32 degree and an effective angle of 29 degree was observed. The switching speed was 90 µs.

The phase transition temperatures of the liquid crystal mixture D were as follows:

Sc 60 Sa 90 N 108 I

Comparative Example 2

In the same manner as described In Example 2, the following compound was mixed in an amount of 20% by weight with the liquid crystal mixture C to prepare a liquid crystal mixture E having similar phase transition temperatures to those of the liquid crystal mixture D.

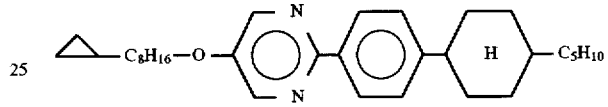

In the same manner as described in Example 1, the resulting liquid crystal mixture E was filled into a cell having a cell thickness of 2 µm, and a rectangular pulse of 30 V at 10 Hz was applied for 30 seconds. The quasi-bookshelf texture having a cone angle of 40 degree and an effective angle of 37 degree was observed. The switching speed was 110 µs.

The phase transition temperatures of the liquid crystal mixture E were as follows:

Sc 50 Sa 86.5 N 93 I

The liquid crystal mixture E comprises typical phenylpyrimidine and phenylbenzoic acid ester compounds, and, as compared with the liquid crystal

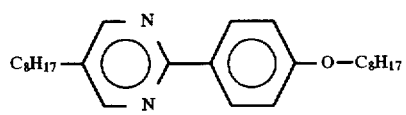 12

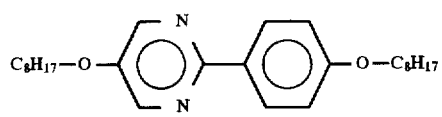 4

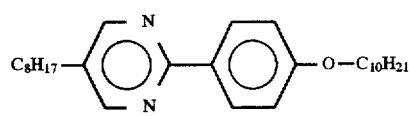 10

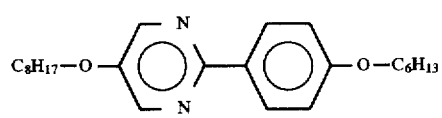 9

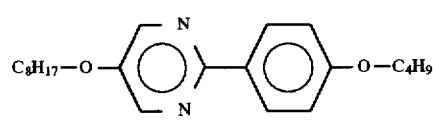 8

-continued

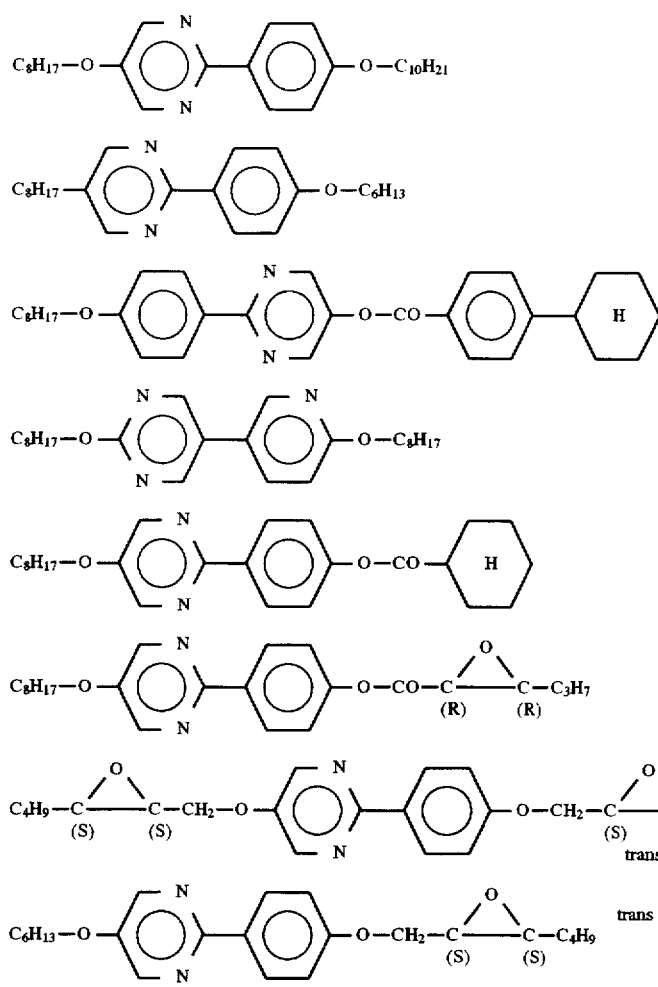

The resulting liquid crystal mixture F was filled into a cell having a cell thickness of 2 μm, and a rectangular pulse of 30 V at 10 Hz was applied for 30 seconds. The quasi-bookshelf texture having a cone angle of 48 degree and an effective angle of 44 degree was observed.

The phase transition temperatures of the liquid crystal mixture B were as follows:

X -8 Sc 63 Sa 79 N 84 I

The compound of the following formula (g), (h) or (i) was mixed with the resulting liquid crystal mixture F In an amount of 8% by weight to prepare liquid crystal mixtures G, H and 1.

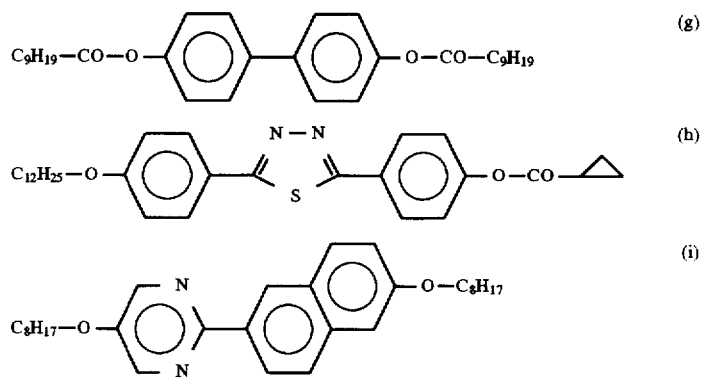

The phase transition temperatures and the cone angle of each of the liquid crystal compositions G, H and I were as follows:

Liquid Crystal Cone
Example Mixture Phase Transition Temperature Angle

33

3 G Sc 63 Sa 78 N 81 I 46
4 H Sc 67 Sa 80 N 86 I 46
I Sc 64 Sa 80 N 86 I 46

EXAMPLE 6

The compounds shown below were mixed with the liquid crystal mixture F obtained in Example 3 at the weight ratio (%) shown below to prepare a liquid crystal mixture J.

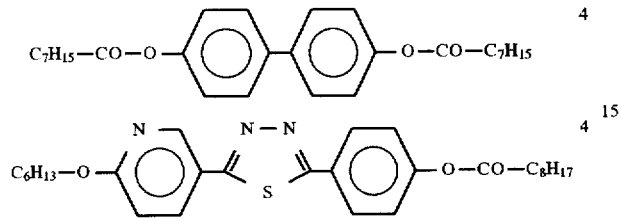

4

4

The cone angle, the effective angle and the phase transition temperatures of the resulting liquid crystal mixture J were as follows:

Cone Angle: 47 degree

Effective Angle: 45 degree

Phase Transition Temperatures: Sc 65 Sa 82 N 84 I

The liquid crystal mixture J containing the specific compounds according to the present invention exhibited an excellent property of reduced cone angle. In spite of the increased phase transition temperatures as compared with the liquid crystal mixture F.

EXAMPLE 7

The compounds shown below were mixed with the liquid crystal mixture F obtained In Example 3 at the weight ratio (%) shown below to prepare a liquid crystal mixture K.

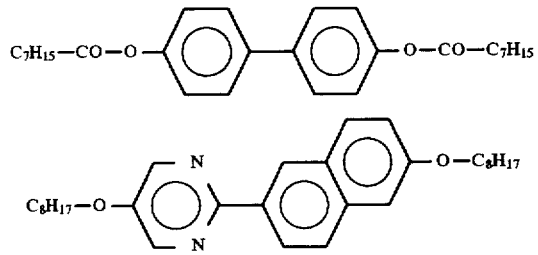

8

8

The cone angle, the effective angle and the phase transition temperatures of the resulting liquid crystal mixture K were as follows:

Cone Angle: 45 degree

Effective, Angle: 43 degree

Phase Transition Temperatures: Sc 63 Sa 79 N 84 I

The liquid crystal mixture K containing the specific compounds according to the present invention exhibited an excellent property of reduced cone angle, in spite of the increased phase transition temperatures as compared with the liquid crystal mixture F.

What is claimed is:

1. A ferroelectric liquid crystal mixture comprising at least one of the compounds of each of the formulae 2 and 3. and having a Sc/Sa phase transition temperature of 60° C. or more and a cone angle of 47 degrees or less at a temperature between 15° C. and 35° C.:

Formula 2:

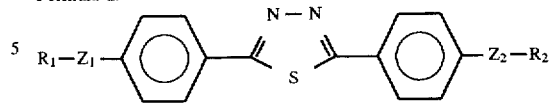

wherein at least one optional =C-H group of the aromatic ring may be substituted with =N—;

$R_1$ and $R_2$ each independently represents (a) a hydrogen atom;

(b) a straight chain or branched chain alkyl group having from 2 to 16 carbon atoms, in which one or two non-adjacent —$CH_2$— groups may be substituted with —O—, —CO—O—, —O—CO—, —Si($CH_3$)$_2$—; and a terminal methyl group may be substituted with a cyclopropyl group; or (c):

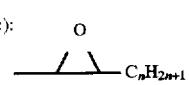

wherein n is an integer of from 1 to 10; and $Z_1$ and $Z_2$ each represents a single bond, —O—, —CO—O—, —O—CO—, —O—$CH_2$— or —$CH_2$—O—; provided that, when $R_1$ is (c), $Z_1$ is —CO—O— or —$CH_2$—O—, and that, when $R_2$ is (c), $Z_2$ is —O—CO—or —$OCH_2$—; and Formula 3:

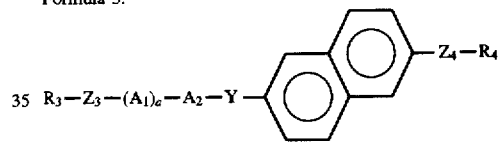

wherein $A_1$ and $A_2$, which may be the same or different, each represents 1,4-phenylene in which one or two hydrogen atoms may be substituted with F or pyridine-2,5-diyl or pyrimidine-2,5-diyl in which one or two hydrogen atoms may be substituted with F;

a is 0 or 1; and $R_3$ and $R_4$ each independently represents (a) a hydrogen atom;

(b) a straight chain or branched chain alkyl group having from 2 to 16 carbon atoms, in which one or two non-adjacent —$CH_2$— groups may be substituted with —O—, —CO—O—, —O—CO—, —Si($CH_3$)$_2$—; and a terminal methyl group may be substituted with a cyclopropyl group; or (c):

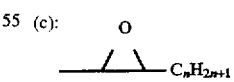

wherein n is an integer of from 1 to 10;

Y is a single bond, —O—CO—, —CO—O—, —O—$CH_2$—or —$CH_2$—O—; and $Z_3$ and $Z_4$ each represents a single bond, —O—, —CO—O—, —O—CO—, —$CH_2$—O— or —O—$CH_2$—; provided that, when $R_3$ is (c), $Z_3$ is —CO—O— or —$CH_2$—O—, and that, when $R_4$ is (c), $Z_4$ is —O—CO— or —O—$CH_2$—.

2. The ferroelectric liquid crystal mixture according to claim 1 comprising at least one of the compounds of each of the formulae 2 and 3, and having a Sc/Sa phase transition temperature of 60° C. or more and a cone angle of 47 degrees or less at a temperature between 15° C and 35° C.:

Formula 2:

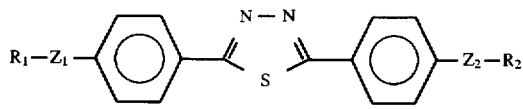

wherein at least one optional =C-H group of the aromatic ring may be substituted with =N—;

$R_1$ and $R_2$ each independently represents:
 (a) a hydrogen atom;
 (b) a straight chain or branched chain alkyl group having from 2 to 16 carbon atoms, in which one or two non-adjacent —$CH_2$— groups may be substituted with —O—, —CO—O—, or —O—CO—; and a terminal methyl group may be substituted with a cyclopropyl group; or (c):

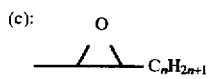

wherein n is an integer of from 1 to 10; and $Z_1$ and $Z_2$ each represents a single bond, —O—, —CO—O—, —O—CO—, —O—CH2— or —$CH_2$—O—; provided that, when $R_1$ is (c), $Z_1$ is —CO—O— or —$CH_2$—O—, and that, when $R_2$ is (c), $Z_2$ is —O—CO— or —0—$CH_2$—; and Formula 3:

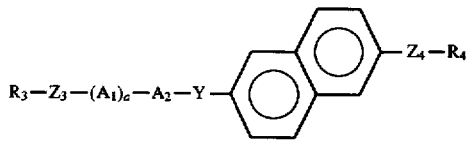

wherein $A_1$ and $A_2$, which may be the same or different, each represents 1,4-phenylene in which one or two hydrogen atoms may be substituted with F or pyridine-2,5-diyl or pyrimidine-2,5-diyl in which one or two hydrogen atoms may be substituted with F;

a is 0 or 1; and $R_3$ and $R_4$ each independently represents:
 (a) a hydrogen atom;
 (b) a straight chain or branched chain alkyl group having from 2 to 16 carbon atoms, in which one or two non-adjacent —$CH_2$— groups may be substituted with —O—, —CO—O—, —O—CO; and a terminal methyl group may be substituted with a cyclopropyl group; or (c):

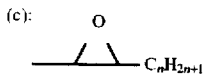

wherein n is an integer of from 1 to 10;

Y is a single bond, —O—CO—, —CO—O—, —O—$CH_2$— or —$CH_2$—O—; and $Z_3$ and $Z_4$ each represents a single bond, —O—, —CO—O—, —O—CO—, —$CH_2$—O— or —O—$CH_2$—; provided that, when $R_3$ is (c), $Z_3$ is —CO—O— or —$CH_2$—O—, and that, when $R_4$ is (c), $Z_4$ is —0—CO— or —O—$CH_2$—.

3. The ferroelectric liquid crystal mixture according to claim 1 comprising at least one of the compounds of each of the formulae 2 and 3, and having a Sc/Sa phase transition temperature of 60° C. or more and a cone angle of 47 degrees or less at a temperature between 15° C. and 35° C.:

Formula 2:

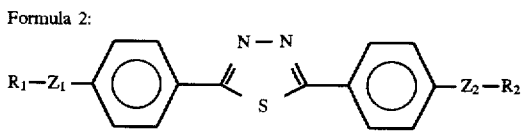

wherein at least one optional =C-H group of the aromatic ring may be substituted with =N—;

$R_1$ and $R_2$ each independently represents:
 (a) a hydrogen atom;
 (b) a straight chain or branched chain alkyl group having from 2 to 16 carbon atoms, in which one or two non-adjacent —$CH_2$— groups may be substituted with —O— and a terminal methyl group may be substituted with a cyclopropyl group; or (c):

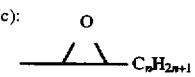

wherein n is an integer of from 1 to 10; and $Z_1$ and $Z_2$ each represents a single bond, or —O—; and Formula 3:

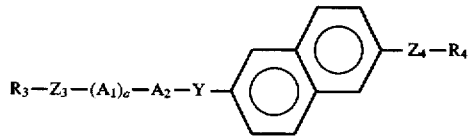

wherein $A_1$ and $A_2$, which may be the same or different, each represents 1,4-phenylene, pyridine-2,5-diyl or pyrimidine-2,5-diyl in which one or two hydrogen atoms may be substituted with F;

a is 0 or 1;

$R_3$ and $R_4$ each independently represents:
 (a) a hydrogen atom;
 (b) a straight chain or branched chain alkyl group having from 2 to 16 carbon atoms, in which one or two non-adjacent —$CH_2$— groups may be substituted with —O—, a chiral epoxy group or —O—CO—O—, and a terminal methyl group may be substituted with a cyclopropyl group; or $R_2$ is a hydrogen atom, a straight or branched chain alkyl group having 2 to 16 carbon atoms or a cyclopropylmethyl group $Z_1$ is —O—

$Z_2$ is a single bond or —O—; and

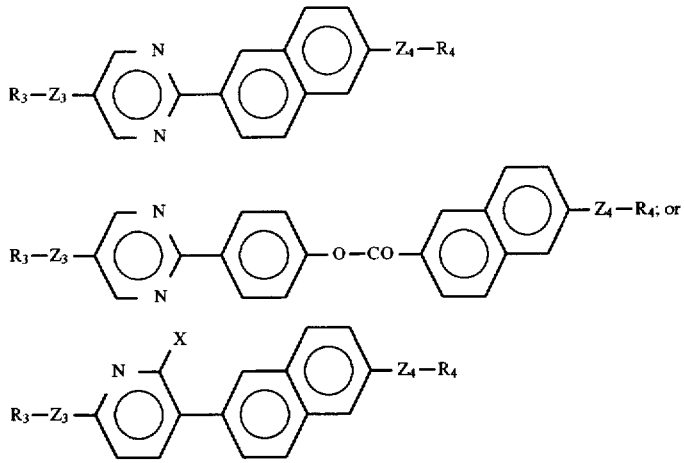

(c): 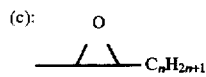

$R_3$ and $R_4$ each independently represents a straight chain or branched alkyl group having 2 to 16 carbon atoms, or

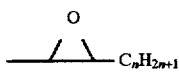

wherein n is an integer of from 1 to 10; Y is a single bond, —O—CO—, —CO—O—, —O—CH$_2$— or —CH$_2$—O—; and $Z_3$ and $Z_4$ each represents a single bond, or —O—.

4. The ferroelectric liquid crystal mixture according to claim 1 comprising at least one of the compounds of each of the formulae 2 and 3, and having a Sc/Sa phase transition temperature of 60° C. or more and a cone angle of 47 degrees or less at a temperature between 15° C. and 35° C.:

where n is an integer from 1 to 10;
X is F or H
$Z_3$ and $Z_4$ are —O—.

5. The ferroeletric liquid crystal mixture according to claim 1 comprising at least one of the compounds of each of the formulae 2 and 3, and having a Sc/Sa phase transition temperature of 60° C. or more and a cone angle of 47 degrees or less at a temperature between 15° C. and 35° C.:

Formula 2:

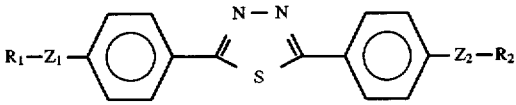

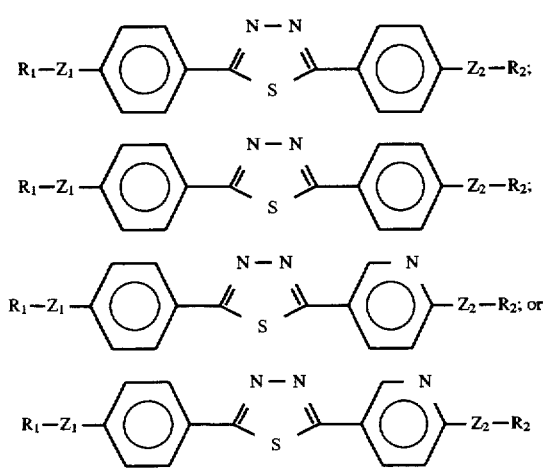

wherein $R_1$ is a straight or branched chain alkyl group having from 2 to 16 carbon atoms;

wherein $R_1$ is a straight chain or branched alkyl group having from 2 to 16 carbon atoms in which one adjacent —CH$_2$— group is substituted with —Si(CH$_3$)$_2$—;

$R_2$ is a straight chain or branched alkyl group having from 2 to 16 carbon atoms;

$Z_1$ is —O—; and $Z_2$ is a single bond.

6. A ferroelectric liquid crystal mixture as claimed in claim 1, comprising from 10% to 50% by weight of a phenyl pyrimidine compound.

7. A ferroelectric liquid crystal display device comprising a ferroelectric liquid crystal mixture as claimed in claim 1.

* * * * *